(12) United States Patent
Thom et al.

(10) Patent No.: US 11,896,830 B2
(45) Date of Patent: *Feb. 13, 2024

(54) SEALED PACKAGE AND METHOD OF FORMING SAME

(71) Applicant: Medtronic, Inc., Minneapolis, MN (US)

(72) Inventors: Andrew J. Thom, Maple Grove, MN (US); Rajesh V. Iyer, Eden Prairie, MN (US); Gordon O. Munns, Stacy, MN (US); Christian S. Nielsen, River Falls, WI (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 399 days.

This patent is subject to a terminal disclaimer.

(21) Appl. No.: 17/164,998

(22) Filed: Feb. 2, 2021

(65) Prior Publication Data

US 2021/0154484 A1    May 27, 2021

Related U.S. Application Data

(63) Continuation of application No. 16/021,177, filed on Jun. 28, 2018, now Pat. No. 10,918,874.

(51) Int. Cl.
*A61N 1/375* (2006.01)
*A61N 1/372* (2006.01)
(Continued)

(52) U.S. Cl.
CPC ....... *A61N 1/37223* (2013.01); *A61N 1/3754* (2013.01); *A61N 1/3758* (2013.01);
(Continued)

(58) Field of Classification Search
CPC ............ A61N 1/37223; A61N 1/37229; A61N 1/375; A61N 1/37518; A61N 1/3754;
(Continued)

(56) References Cited

U.S. PATENT DOCUMENTS 3,835,864 A    9/1974  Rasor et al.
4,991,582 A    2/1991  Byers et al.
(Continued)

FOREIGN PATENT DOCUMENTS

WO    2017/015248    1/2017

*Primary Examiner* — George Manuel
(74) *Attorney, Agent, or Firm* — Mueting Raasch Group (57) ABSTRACT

Various embodiments of a hermetically-sealed package and a method of forming such package are disclosed. The package includes a housing that extends along a housing axis between a first end and a second end, where the housing includes first and second opaque portions and a transparent portion disposed between the first and second opaque portions. The first opaque portion is hermetically sealed to a first end of the transparent portion and the second opaque portion is hermetically sealed to a second end of the transparent portion. At least one of the first and second opaque portions is hermetically sealed to the transparent portion by a weld ring. The package further includes a power source disposed within the housing, and an inductive coil disposed at least partially within the transparent portion of the housing and electrically connected to the power source.

20 Claims, 7 Drawing Sheets

(51) Int. Cl.
*H02J 50/10* (2016.01)
*H02J 7/00* (2006.01)
*H02J 50/00* (2016.01)

(52) U.S. Cl.
CPC ...... *A61N 1/37518* (2017.08); *H02J 7/00034* (2020.01); *H02J 50/10* (2016.02); *H02J 50/005* (2020.01)

(58) Field of Classification Search
CPC .. A61N 1/3758; A61N 1/3787; A61N 1/3968; H02J 2310/23; H02J 50/005; H02J 50/10; H02J 7/00034; H04B 5/0037; H04B 5/0075
See application file for complete search history.

(56) References Cited

U.S. PATENT DOCUMENTS

| | | | |
|---|---|---|---|
| 5,470,345 A | 11/1995 | Hassler et al. | |
| 5,902,326 A | 5/1999 | Lessar et al. | |
| 6,850,803 B1 | 2/2005 | Jimenez et al. | |
| 7,174,212 B1 | 2/2007 | Klehn et al. | |
| 8,253,555 B2 | 8/2012 | Stevenson et al. | |
| 8,401,648 B2 | 3/2013 | Kast et al. | |
| 8,433,409 B2 | 4/2013 | Johnson et al. | |
| 8,541,131 B2 | 9/2013 | Lund et al. | |
| 9,120,287 B2 | 9/2015 | Ruben et al. | |
| 9,171,721 B2 | 10/2015 | Danzl et al. | |
| 9,511,236 B2 | 12/2016 | Varady et al. | |
| 9,688,053 B2 | 6/2017 | Ruben et al. | |
| 2009/0156905 A1 | 6/2009 | Ries et al. | |
| 2009/0171420 A1 | 7/2009 | Brown et al. | |
| 2010/0060431 A1* | 3/2010 | Stevenson | A61B 5/0031 340/10.1 |
| 2010/0191306 A1 | 7/2010 | Stevenson et al. | |
| 2011/0102967 A1 | 5/2011 | Munns et al. | |
| 2011/0249381 A1 | 10/2011 | Diebold | |
| 2015/0066113 A1 | 3/2015 | Van Funderburk | |
| 2015/0080982 A1 | 3/2015 | Van Funderburk | |
| 2015/0321012 A1 | 11/2015 | Cinbis et al. | |
| 2016/0185081 A1 | 6/2016 | Sandlin et al. | |
| 2016/0296760 A1 | 10/2016 | Sahabi et al. | |
| 2017/0100597 A1 | 4/2017 | Barror et al. | |
| 2017/0127543 A1 | 5/2017 | Day et al. | |

\* cited by examiner

SEALED PACKAGE AND METHOD OF FORMING SAME

RELATED APPLICATIONS

This application is a continuation of U.S. patent application Ser. No. 16/021,177, filed Jun. 28, 2018, which is incorporated herein by reference.

BACKGROUND

Various systems require electrical coupling between electrical devices disposed within a hermetically sealed enclosure and external devices. Oftentimes, such electrical coupling needs to withstand various environmental factors such that a conductive pathway or pathways from an external surface to within the enclosure remains stable. For example, implantable medical devices (IMDs), e.g., cardiac pacemakers, defibrillators, neurostimulators, and drug pumps, which can include electronic circuitry and battery elements, require an enclosure or housing to contain and hermetically seal these elements when the IMD is disposed within a body of a patient. Many of these IMDs include one or more electrical feedthrough assemblies to provide electrical connections between the elements contained within the housing and components of the IMD external to the housing. For example, one or more sensors, electrodes, and lead wires can be mounted on an exterior surface of the housing and electrically connected to one or more elements disposed within the housing. Further, electrical contacts can be housed within a connector header that is mounted on the housing to provide coupling for one or more implantable leads, which typically carry one or more electrodes or other types of physiological sensors. A physiological sensor, for example a pressure sensor, incorporated within a body of a lead may also require a hermetically sealed housing to contain electronic circuitry of the sensor and an electrical feedthrough assembly to provide electrical connection between one or more lead wires, which extend within the implantable lead body, and the contained circuitry.

An IMD can also include one or more transparent portions that can provide a window for transmission of electromagnetic radiation into and out of the housing. For example, an IMD can include an optical sensor that transmits and receives electromagnetic radiation through a transparent window disposed in the housing. Such transparent window typically includes a nonconductive material that is connected to one or more conductive portions of the housing such that the window is hermetically-sealed to the conductive portions.

SUMMARY

In general, the present disclosure provides various embodiments of a hermetically-sealed package and a method of forming such package. The package can include a housing that has a transparent portion that is connected to at least one opaque portion. The package can also include a power source disposed within the housing and an inductive coil also disposed within the housing such that at least a portion of the inductive coil is disposed within the transparent portion. The inductive coil can be electrically connected to the power source. In one or more embodiments, an inductive charging system can be utilized to charge the power source via the inductive coil. For example, the hermetically-sealed package can be utilized as an implantable medical device that can be implanted within a patient's body and charged while implanted.

In one aspect, the present disclosure provides a hermetically-sealed package that includes a housing that extends along a housing axis between a first end and a second end, where the housing includes first and second opaque portions and a transparent portion disposed between the first and second opaque portions. The first opaque portion is hermetically sealed to a first end of the transparent portion, and the second opaque portion is hermetically sealed to a second end of the transparent portion. At least one of the first and second opaque portions is hermetically sealed to the transparent portion by a weld ring. The package further includes a power source disposed within the housing and an inductive coil disposed at least partially within the transparent portion of the housing and electrically connected to the power source.

In another aspect, the present disclosure provides a housing assembly that includes a housing having an outer surface and extending along a housing axis between a first end and a second end, and a weld ring compression bonded to the outer surface of the housing such that the weld ring is hermetically-sealed to the outer surface of the housing.

In another aspect, the present disclosure provides a method of forming a hermetically-sealed package that includes a housing that extends along a housing axis between a first end and a second end. The method includes compression bonding a weld ring to an outer surface of a transparent portion of the housing. Compression bonding the weld ring includes heating the weld ring, disposing the weld ring over the outer surface of the transparent portion of the housing, and cooling the weld ring.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure provides various embodiments of a hermetically-sealed package and a method of forming such package. The package can include a housing that has a transparent portion that is connected to at least one opaque portion. The package can also include a power source disposed within the housing and an inductive coil also disposed within the housing such that at least a portion of the inductive coil is disposed within the transparent portion. The inductive coil can be electrically connected to the power source. In one or more embodiments, an inductive charging system can be utilized to charge the power source via the inductive coil. For example, the hermetically-sealed package can be utilized as an implantable medical device that can be implanted within a patient's body and charged while implanted.

In one or more embodiments, the hermetically-sealed package can be formed using low-temperature techniques that do not require the use of high-temperature brazing materials. Further, in one or more embodiments, the hermetically-sealed package can be formed without creating unacceptable stresses in the materials used to form the package that can be caused by use of high-temperature bonding techniques to connect one or more transparent portions to one or more conductive portions of the housing of the package. For example, one or more embodiments of hermetically-sealed packages described herein can be formed utilizing a low-temperature compression bonding technique to connect one or more weld rings to the transparent portion of the housing. Such weld rings can also be utilized to connect one or more opaque portions to the transparent portion using any suitable technique, e.g., welding, laser welding, diffusion bonding, laser-assisted diffusion bonding, etc.

Figure 1:
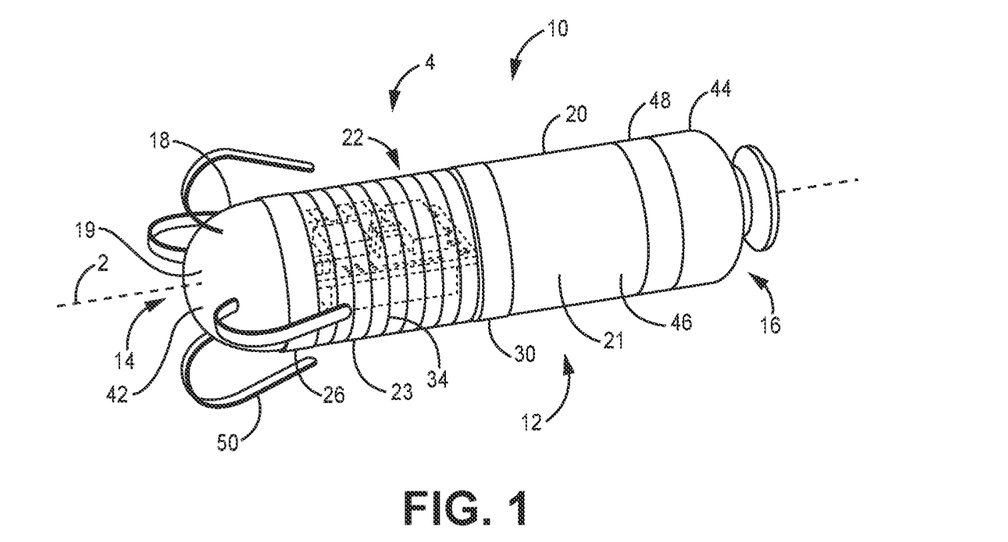
FIG. 1 is a schematic perspective view of one embodiment of a hermetically-sealed package.
Figure 2:
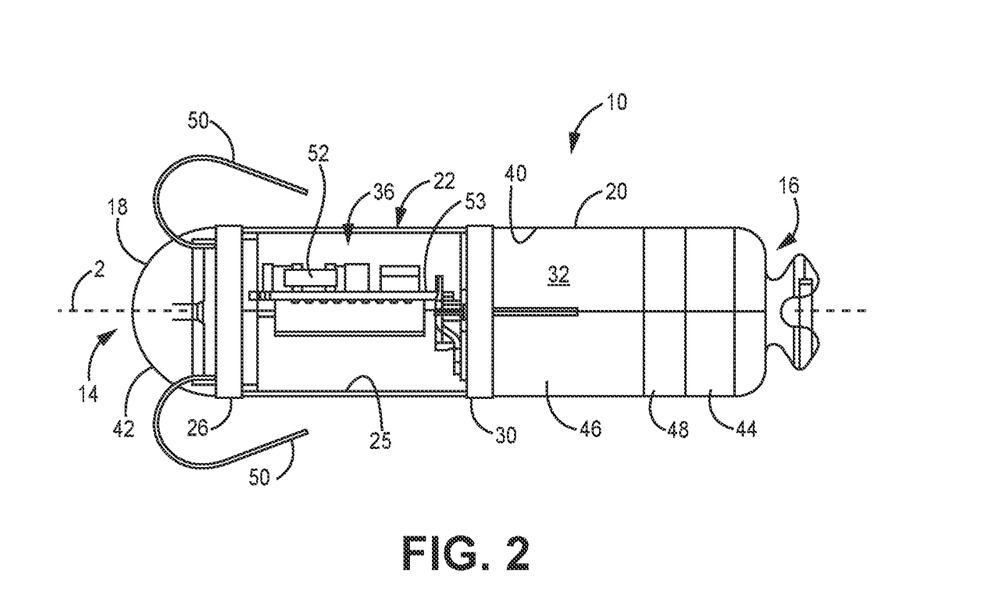
FIG. 2 is a schematic cross-section view of the hermetically-sealed package of FIG. 1.
Figure 3:
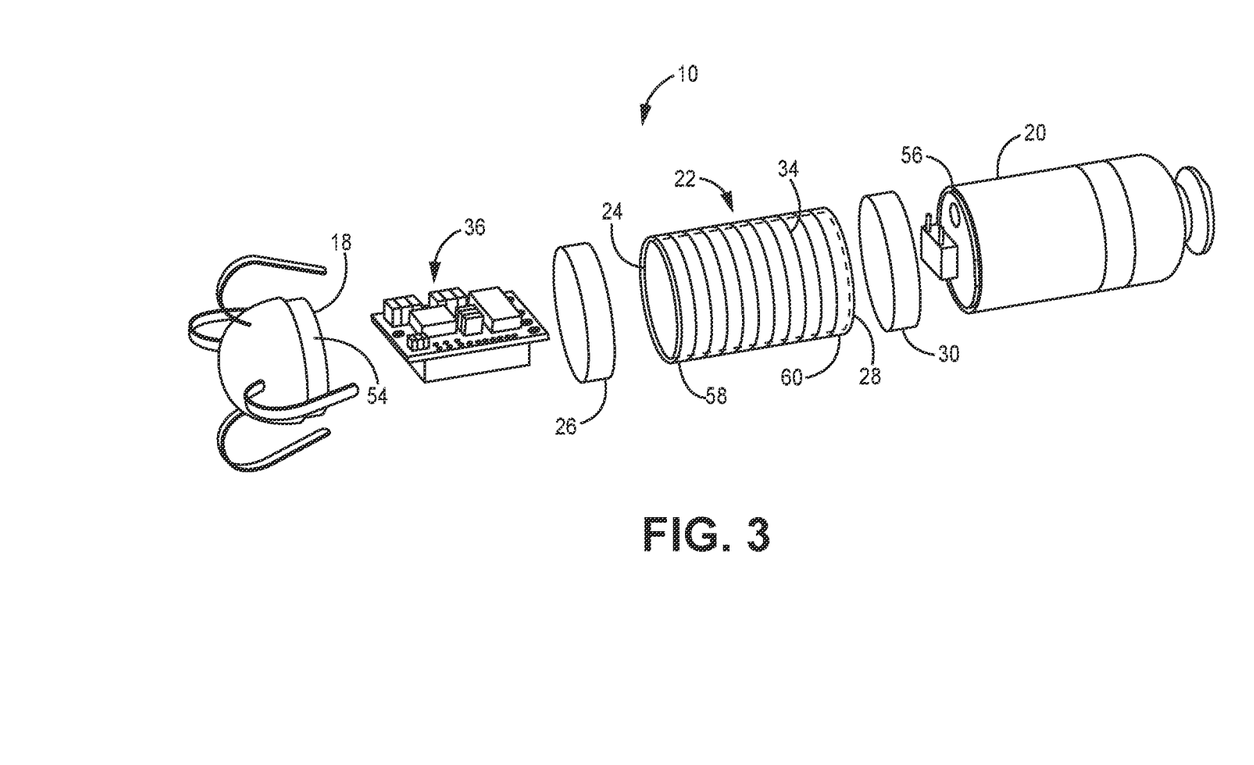
FIG. 3 is a schematic exploded view of the hermetically-sealed package of FIG. 1.

FIGS. 1-3 are various views of one embodiment of a hermetically-sealed package 10. The package 10 includes a housing 12 that extends along a housing axis 2 between a first end 14 and a second end 16. The housing 12 includes first and second opaque portions 18, 20 and a transparent portion 22 disposed between the first and second opaque portions. In one or more embodiments, the first opaque portion 18 is hermetically sealed to a first end 24 of the transparent portion 22, and the second opaque portion 20 is hermetically sealed to a second end 28 of the transparent portion. At least one of the first and second opaque portions 18, 20 is hermetically sealed to the transparent portion 22 by a weld ring (e.g., first weld ring 26 and/or second weld ring 30). The hermetically-sealed package 10 also includes a power source 32 (FIG. 2) disposed within the housing 12 and an inductive coil 34 disposed at least partially within the transparent portion 22 of the housing 12 and electrically connected to the power source.

In general, the housing 12 can have any suitable dimensions, e.g., the housing can have any suitable length as measured in a direction parallel to the housing axis 2 between the first end 14 and the second end 16. Further, each of the first and second opaque portions 18, 20 and the transparent portion 22 can have any suitable dimensions.

The housing 12 includes the first and second opaque portions 18, 20. Although depicted as including two opaque portions 18, 20, the housing 12 can include any suitable number of opaque portions, e.g., one, two, three, four, or more opaque portions. For example, in one or more embodiments, the housing 12 can include one opaque portion that is connected to either the first end 24 or the second end 28 of the transparent portion 22.

The first and second opaque portions 18, 20 can take any suitable shape or shapes. For example, at least one of the first and second opaque portions 18, 20 can take any suitable shape in a plane orthogonal to the housing axis 2. In the embodiment illustrated in FIGS. 1-3, each of the first and second opaque portions 18, 20 takes an elliptical (e.g., circular) shape in the plane orthogonal to the housing axis 2. Each of the first and second opaque portions 18, 20 can also have an area in the plane orthogonal to the housing axis 2 that is constant or varies in a direction parallel to the housing axis. For example, as shown in FIG. 1, the first opaque portion 18 has an area in the plane orthogonal to the housing axis 2 that decreases in a direction from the second end 16 of the housing to the first end 14. Further, for example, the first and second opaque portions 18, 20 can take any suitable shape or shapes in a plane parallel to the housing axis 2. In the illustrated embodiment, the first opaque portion 18 takes a curved shape in the plane parallel to the housing axis 2, and the second opaque portion 20 takes a rectangular shape in the plane parallel to the housing axis.

One or more portions of the at least one of the first and second opaque portions 18, 20 can be hollow to provide a cavity having any suitable dimensions. In one or more embodiments, at least one of the first and second opaque portions 18, 20 can be solid.

The first and second opaque portions 18, 20 can include any suitable material or materials, e.g., metal, polymeric, ceramic, or inorganic materials. In one or more embodiments, the first and second opaque portions 18, 20 can include at least one of glass, quartz, silica, sapphire, silicon carbide, diamond, and gallium nitride. In one or more embodiments, the first and second opaque portions 18, 20 can include at least one of copper, silver, titanium, niobium, zirconium, tantalum, stainless steel, platinum, iridium. Further, in one or more embodiments, the first and second opaque portions 18, 20 can include biocompatible materials such that the package 10 can be implanted within a patient's body. Further, one or more coatings or layers can be disposed on outer surfaces of the first and second opaque portions 18, 20 that provide biocompatibility. In one or more embodiments, at least one of the first and second opaque portions 18, 20 can be electrically conductive to provide a ground electrode for the package 10 as is known in the art. In one or more embodiments, one or more portions of the first and second opaque portions 18, 20 can be nonconductive.

Further, at least a portion of the housing 12 can be substantially transmissive at a desired wavelength or range of wavelengths or a desired frequency or range of frequencies. For example, in the embodiment illustrated in FIGS. 1-3, the housing 12 includes the transparent portion 22 disposed between the first and second opaque portions 18, 20. As used herein, the term "transparent" means that one or more portions of the housing transmits to electromagnetic radiation of any desired wavelength or frequency. For example, in one or more embodiments, the transparent portion 22 can be transparent to radio-frequency (RF) electromagnetic radiation.

Although depicted as including one transparent portion 22, the housing 12 can include any suitable number of transparent portions. In one or more embodiments, the transparent portion 22 can be disposed within one or both of the first and second opaque portions 18, 20. Further, the transparent portion 22 can take any suitable shape or shapes and have any suitable dimensions. In the embodiment illustrated in FIGS. 1-3, the transparent portion 22 takes an elliptical (e.g., circular) shape in the plane orthogonal to the housing axis 2. The transparent portion 22 can have a constant area in the plane perpendicular to the housing axis 2 or an area that changes in a direction parallel to the housing axis. Further, the transparent portion 22 can take a rectangular shape in the plane parallel to the housing axis 2.

The transparent portion 22 of the housing 12 can include any suitable material or materials that are substantially transmissive to one or more wavelengths or frequencies of electromagnetic radiation, e.g., at least one of glass, quartz, silica, sapphire, silicon carbide, diamond, and gallium nitride. In one or more embodiments, the transparent portion 22 can include a ceramic material. Further, in one or more embodiments, the transparent portion 22 can include a nonconductive (i.e., dielectric) material.

As used herein, the phrase "substantially transmissive" means that the transparent portion 22 transmits greater than 50% of electromagnetic radiation incident on the transparent portion for a selected wavelength or range of wavelengths, or a selected frequency or range of frequencies. In one or more embodiments, the transparent portion 22 can be substantially transmissive to electromagnetic radiation having a frequency in a range of 10 kHz to 20 MHz. In one or more embodiments, the transparent portion 22 can be substantially transmissive to at least one of UV light, visible light, and IR light. In one or more embodiments, the transparent portion 22 can be substantially transmissive such that the electronic devices 36 can include one or more optical sensors that can be utilized to detect one or more preselected external conditions, e.g., blood oxygen levels. In one or more embodiments, the transparent portion 22 can be substantially transmissive to radio-frequency (RF) electromagnetic radiation such that the package 10 can be remotely charged utilizing an RF charging system as is further described herein.

In one or more embodiments, one or more portions of the transparent portion 22 can be hollow to provide a cavity or cavities having any suitable dimensions. In one or more embodiments, the transparent portion 22 can be solid.

The first and second opaque portions 18, 20 can be connected to the transparent portion 22 using any suitable technique or techniques. In one or more embodiments, the first opaque portion 18 can be connected to the transparent portion 22 by the first weld ring 26. Further the second opaque portion 20 can be connected to the transparent portion 22 by the second weld ring 30. The housing 12, transparent portion 22, first weld ring 26, and second weld ring 30 combine to provide a housing assembly 4. Although depicted as including the first and second weld rings 26, 30, the assembly 10 can include only the second weld ring, and the first opaque portion 18 can be connected to the transparent portion 22 using any suitable technique or techniques, e.g., welding, laser welding, diffusion bonding, laser-assisted diffusion bonding, etc., without the use of the first weld ring. For example, in one or more embodiments, the first opaque portion 18 can be connected to the transparent portion 22 by a feedthrough header plate that is diffusion bonded to the transparent portion. Similarly, in one or more embodiments, the assembly 10 can include only the first weld ring 26, and the second opaque portion 20 can be connected to the transparent portion 22 using any suitable technique or techniques, e.g., welding, laser welding, diffusion bonding, laser-assisted diffusion bonding, etc., without the use of the second weld ring.

The weld rings 26, 30 can include any suitable material or materials, e.g., copper, silver, titanium, niobium, zirconium, tantalum, stainless steel, platinum, iridium, and combinations thereof. In one or more embodiments, the weld rings 26, 30 can include two or more materials, e.g., bi-metals, clad laminates, etc. In one or more embodiments, the weld rings 26, 30 can include any suitable bio-compatible and weldable materials. Further, the weld rings 26, 30 can take any suitable shape and have any suitable dimensions. In one or more embodiments, the first weld ring 26 can be hermetically sealed to one or both of the transparent portion 22 and the first opaque portion 18. Further, in one or more embodiments, the second weld ring 30 can be hermetically sealed to one or both of the transparent portion 22 and the second opaque portion 20.

The weld rings 26, 30 can be sealed to the opaque portions 18, 20 and the transparent portion 22 using any suitable technique or techniques, e.g., diffusion bonding, laser diffusion bonding, compression bonding. In one or more embodiments, the weld rings 26, 30 are first connected to the transparent portion 22 and then attached to the respective opaque portions 18, 20.

The first weld ring 26 can be connected to any suitable portion or portions of the transparent portion 22 and any suitable portion or portions of the first opaque portion 18. Similarly, the second weld ring 30 can be connected to any suitable portion or portions of the transparent portion 22 and any suitable portion or portions of the second opaque portion 20. In one or more embodiments, one or both of the first and second weld rings 26, 30 can be connected to an outer surface 23 of the transparent portion 22. Further, in one or more embodiments, the first weld ring 26 can be connected to an outer surface 19 of the first opaque portion 18, and the second weld ring 30 can be connected to an outer surface 21 of the second opaque portion 20.

In one or more embodiments, at least one of the first and second weld rings 26, 30 can include a flange or recessed portion that is adapted to mate with a flange or recessed portion of one or both of the opaque portions 18, 20 and the transparent portion 22. For example, the first weld ring 26 can be connected to a flange 54 (FIG. 3) of the first opaque portion 18 and a flange 58 of the transparent portion 22. Further, the second weld ring 30 can be connected to a flange 56 of the second opaque portion 20 and a flange 60 of the transparent portion 22.

Figure 4:
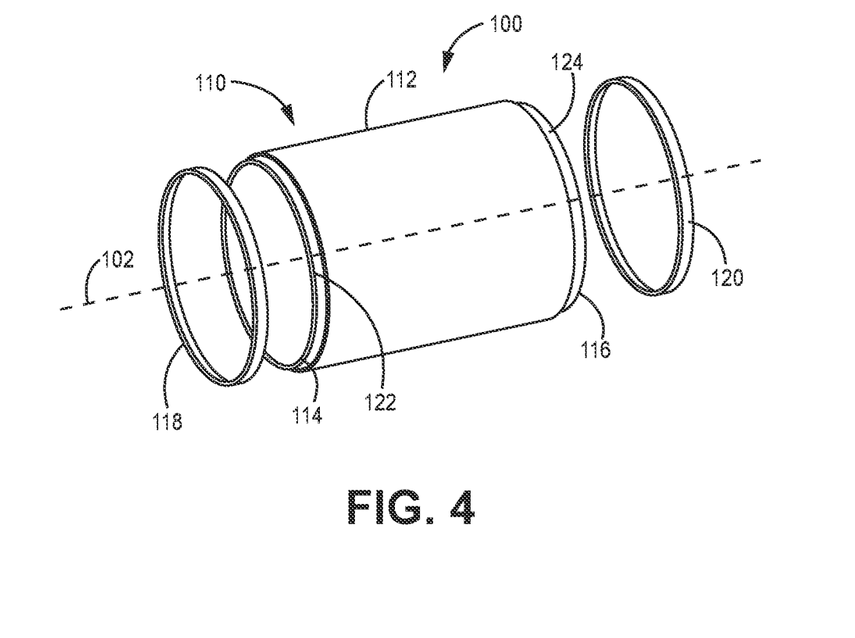
FIG. 4 is a schematic exploded view of one embodiment of a housing assembly.
Figure 5:
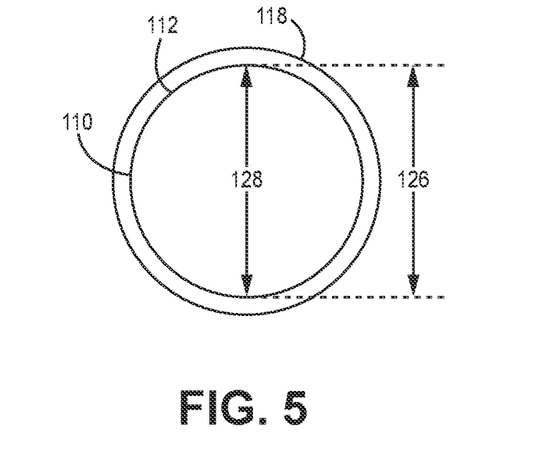
FIG. 5 is a schematic cross-section view of the housing assembly of FIG. 4.

Further, for example, FIGS. 4-5 are various views of one embodiment of a housing assembly 100. The housing assembly 100 can be utilized with any suitable device or system, e.g., the hermetically-sealed package 10 of FIGS. 1-3. All of the design considerations and possibilities regarding the housing assembly 4 of FIGS. 1-3 apply equally to the housing assembly 100 of FIGS. 4-5.

The housing assembly 100 includes a housing 110 that has an outer surface 112 and extends along a housing axis 102 between a first end 114 and a second end 116 of the housing. The housing 110 can include any suitable number of transparent portions and opaque portions. The assembly 100 also includes a first weld ring 118 connected to the outer surface 112 of the housing 110. In one or more embodiments, the assembly 100 also includes a second weld ring 120 also connected to the outer surface 112 of the housing 110. Although depicted as including two weld rings 118, 120, the assembly 100 can include any suitable number of weld rings. For example, in one or more embodiments, the assembly includes the first weld ring 118 and not the second weld ring 120 or vice versa.

The housing 110 can include any suitable material or materials, e.g., the materials described herein regarding the first and second opaque portions 18, 20 and the transparent portion 22 of the package 10 of FIGS. 1-3. Further, the weld rings 118, 120 can include any suitable material or materials, e.g., the materials described herein regarding weld rings 26, 30 of package 10 of FIGS. 1-3.

In one or more embodiments, the housing 110 can include a flange 122 disposed adjacent to the first end 114 of the housing. As used herein, the term "adjacent to the first end of the housing" means that an element or component is disposed closer to the first end 114 of the housing 110 than to the second end 116 of the housing. Further, the housing 110 includes a second flange 124 disposed adjacent to the second end 116 of the housing. As used herein, the term "adjacent to the second end of the housing" means that an element or component is disposed closer to the second end 116 of the housing 110 than to the first 114 end of the housing. The flanges 122, 124 can be adapted such that the weld rings 118, 120 can be disposed over the flanges and connected to the housing 110 using any suitable technique or techniques. In one or more embodiments, one or both of the weld rings 118, 120 can be compression bonded to the outer surface 112 of the housing 110 as is further described herein. In one or more embodiments, the weld rings 118, 120 can be connected to the outer surface 112 of the housing 110 such that the weld rings are hermetically sealed to the outer surface of the housing. In one or more embodiments, a diffusion layer (not shown) can be disposed between one or both of the weld rings 118, 120 and the outer surface 112 of the housing 110 that is formed when the weld rings are compression bonded to the outer surface of the housing. Such diffusion layer can have any suitable thickness. Although not shown, one or more crush ribs can be disposed on one or both flanges 122, 124 that are adapted to at least partially collapse when the weld rings 118, 120 are disposed onto the flanges.

The weld rings 118, 120 can each have an inner diameter 126 as shown in FIG. 5, which is an end view of the housing assembly 100 of FIG. 4 and illustrates the first weld ring 118 connected to the outer surface 112 of the housing 110. As shown in FIG. 5, the housing 110 has an outer diameter 128 where the weld rings 118, 120 are connected. In one or more embodiments, the inner diameter 126 of each of the weld rings 118, 120 can be greater than the outer diameter 128 of the outer surface 112 of the housing 110 at the portion of the housing that is connected to the weld rings.

In one or more embodiments, one or both of the weld rings 118, 120 can be compression bonded to the housing 110. Such compression bonding can be applied to a region of the housing 110 that includes notched or flanged edges as one or both of the weld rings 118, 120 are connected to the housing using heat shrink techniques.

In one or more embodiments, a thin metal film or layer (e.g., titanium or niobium) may be applied to the bonding surface of the housing 110, and any suitable bonding technique can be utilized to bond one or both of the weld rings 118, 120 to the housing such that the thin metal film or layer is disposed between the weld rings and the transparent portion. In one or more embodiments, the thin metal film or layer can assist with bonding between the weld rings 118, 120 and the housing 110. The thin metal film or layer can have any suitable thickness, e.g., at least 500 nm and no greater than 5000 nm.

A compression force can be applied axially to the assembly 100 to assist in connecting the first and second weld rings 118, 120 to the housing 110. In one or more embodiments, the first and second weld rings 118, 120 are hermetically sealed to the housing 110 of the housing assembly 100. In one or more embodiments, the weld rings 118, 120 can be utilized to connect the housing 110 to one or more additional transparent or opaque portions utilizing any suitable technique or techniques.

Figure 6:
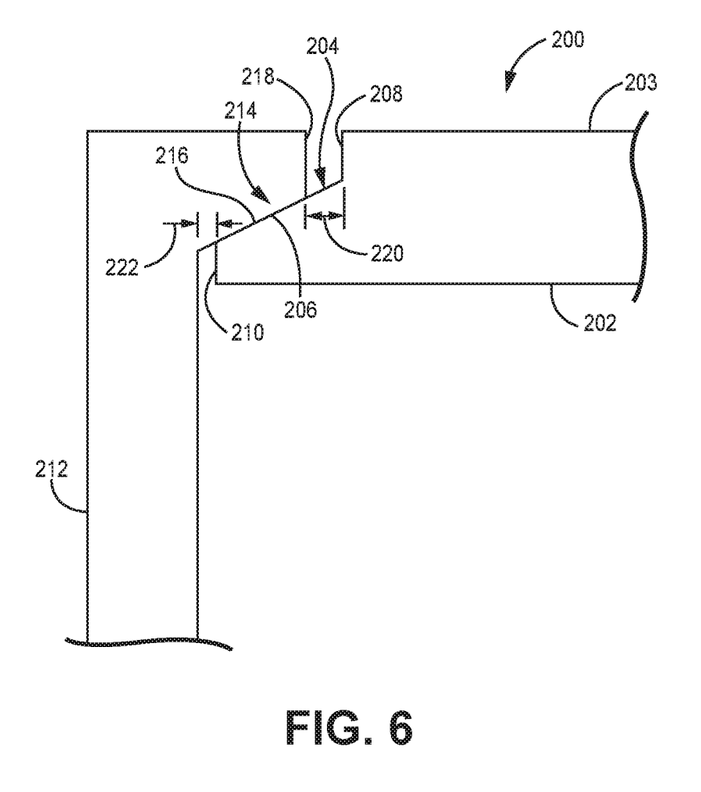
FIG. 6 is a schematic cross-section view of a portion of another embodiment of a housing assembly.

The flanges 122, 124 of the housing 110 can take any suitable shape and have any suitable dimensions. In one or more embodiments, one or both of the weld rings 118, 120 can also include a flange that is adapted to be received by the flanges 122, 124 of the housing 110. For example, FIG. 6 is a schematic cross-section view of a portion of a housing assembly 200. All of the design considerations and possibilities regarding the housing assembly 100 of FIGS. 4-5 apply equally to the housing assembly 200 of FIG. 6.

The housing assembly 200 includes a housing 202 and a weld ring 212. Housing 202 includes a flange 204 that has a tapered portion 206. Further, the weld ring 212 has a flange 214 that includes a tapered portion 216. The tapered portion 206 of the flange 204 of the housing 202 is adapted to receive the tapered portion 216 of the flange 214 of the weld ring 212. The tapered portions 206, 216 are adapted to allow the weld ring 212 to more easily slide onto an outer surface 203 of the housing 202. In one or more embodiments, a gap 220 can be formed between a straight portion 218 of the flange 214 of the weld ring 212 and a straight portion 208 of the flange 204 of the housing 202. Further, in one or more embodiments, a gap 222 can be formed between the weld ring 212 and an end 210 of the housing 202. Each of the gaps 220, 222 can be any suitable length.

Any suitable technique or techniques can be utilized to connect the weld ring 212 to the housing, e.g., welding, laser welding, bonding, diffusion bonding, laser assisted diffusion bonding, etc. In one or more embodiments, the weld ring 212 can be hot press thermal diffusion bonded to the housing 202 as is further described herein.

Figure 7:
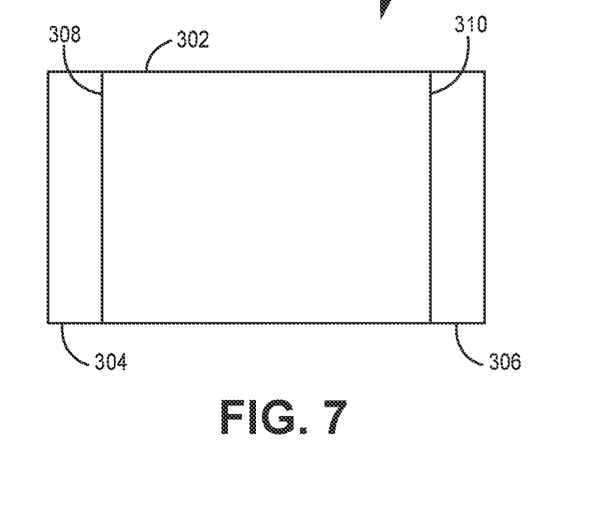
FIG. 7 is a schematic front view of another embodiment of a housing assembly.

As stated herein, a weld ring can be connected to transparent and opaque portions of a housing using any suitable technique or techniques. In one or more embodiments, one or more weld rings can be connected to the housing using a butt joint. For example, FIG. 7 is a schematic front view of another embodiment of a housing assembly 300. All of the design considerations and possibilities regarding the housing assembly 100 of FIGS. 4-5 apply equally to the housing assembly 300 of FIG. 7. The housing assembly 300 includes a housing 302 connected to a first weld ring 304 and second weld ring 306. The first weld ring 304 is connected to the housing 302 adjacent to a first end 308 of the portion, and the second weld ring 306 is connected to the housing 302 adjacent to a second end 310 of the housing.

A side surface of the first end 308 of the housing 302 is connected to a side surface of the first weld ring 304. Further, a side surface of the second end 310 of the housing 302 is connected to a side surface of the second weld ring 306. Any suitable technique or techniques can be utilized to connect the weld rings 304, 306 to the housing 302, e.g., welding, laser welding, bonding, diffusion bonding, laser assisted diffusion bonding, etc. In one or more embodiments, the weld rings 304, 306 can be diffusing bonded to the housing 302 using any suitable diffusion bonding technique. For example, hot press thermal diffusion bonding can be used for various edge surfaces on the housing 302, e.g., butt joint, notched edges, tapered edges, etc. A uniaxial load (e.g., 1-4 Megapascals) can be applied to the weld rings 304, 306 and the housing using any suitable technique at a temperature of 600-1000° C. for any suitable time period, e.g., at least 10 minutes to no greater than 10 hours, under a high vacuum or inert gas such as argon.

Figure 8:
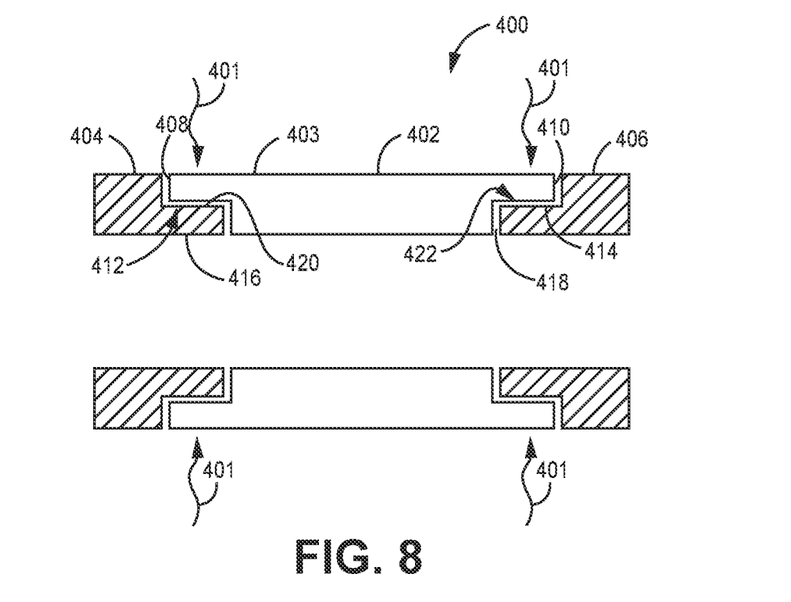
FIG. 8 is a schematic cross-section view of a portion of another embodiment of a housing assembly.

As mentioned herein, one or both of the housing and weld rings of the housing assemblies described herein can include a flange. For example, FIG. 8 is a schematic cross-section of another embodiment of housing assembly 400. All of the design considerations and possibilities regarding the housing assembly 100 of FIGS. 4-5 apply equally to the housing assembly 400 of FIG. 8. The assembly 400 includes a housing 402 and first and second weld rings 404, 406. The housing 402 can include one or more transparent portions, e.g., transparent portion 22 of FIG. 1. In one or more embodiments, the entire housing 402 is transparent to any suitable wavelength or wavelengths. The first weld ring 404 is connected to the housing 402 adjacent to a first end 408 of the housing, and a second weld ring 406 is connected to the housing adjacent to a second end 410 of the housing.

The first end 408 of the housing 402 includes a flange 412 that is adapted to mate with a flange 416 of the first weld ring 404. Further, the second end 410 of the housing 402 includes a flange 414 that is adapted to mate with a flange 418 of the second weld ring 406. The first and second weld rings 404, 406 can be connected to the housing 402 of the housing assembly 400 using any suitable technique or techniques.

In general, the weld rings 404, 406 can be hermetically sealed to the housing 402 by a bond. Any suitable technique or techniques can be utilized to form such bond, e.g., laser diffusion bonding at an interface 420 between flange 412 of the housing 402 and the flange 416 of the first weld ring 420, thermal diffusion bonding between flanges 414, 416 and the housing, etc. In one or more embodiments, one or both of the weld rings 404, 406 can be hermetically sealed to the housing 402 utilizing the laser diffusion bonding techniques described in co-owned and co-filed U.S. Patent Publication No. 2016/0185081, entitled KINETICALLY LIMITED NANO-SCALE DIFFUSION BOND STRUCTURES AND METHODS. For example, electromagnetic radiation 401 (e.g., light) can be directed through the housing 402 (e.g., a transparent portion of the housing) from its outer surface 403 and focused at an interface 420 between the flange 412 of the housing and the flange 416 of the first weld ring 404. Further, electromagnetic radiation can be directed through the housing 402 from the outer surface 403 and focused at an interface 422 between the flange 414 of the housing and the flange 418 of the second weld ring 406. In one or more embodiments, a uniaxial load may be applied during the laser bonding process to maintain contact between the weld rings 404, 406 and the housing 402.

Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 10,000 nm. For example, laser light can include UV light, visible light, IR light, and combinations thereof. In one or more embodiments, a UV laser can be utilized to provide light having a wavelength of about 300 nm and a pulse width of 10 ns. In one or more embodiments, the materials for the housing 402 and the weld rings 404, 406, and the power level and wavelength of the light used may be selected such that the light may not directly damage, ablate, warp, or cut the external contacts and the housing, and such that the external contacts and the housing retain their bulk properties.

In general, light can be provided by any suitable laser or laser system. For example, the laser may generate light having a relatively narrow set of wavelengths (e.g., a single wavelength). The light emitted by the laser may form a collimated beam that may not be focused at a particular point. The light emitted by the laser may be focused at the interfaces 416, 418 to generate a laser bond.

Although the laser may provide light that has a narrow range of wavelengths, in one or more embodiments, the laser may represent one or more devices that emit light having a wider range of wavelengths than a single typical laser. A wide variety of devices may be used to emit light having a narrow or wide range of wavelengths. In one or more embodiments, the laser may include one or more laser devices including diode and fiber lasers. Laser sources may also include, e.g., TI sapphire, argon ion, Nd:YAG, XeF, HeNe, Dye, GaAs/AlGaAs, $CO_2$, Alexandrite, InGaAs, InGaAsP, Nd:glass, Yb:YAG, or Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat or Gaussian spatial energy profile.

Figure 9:
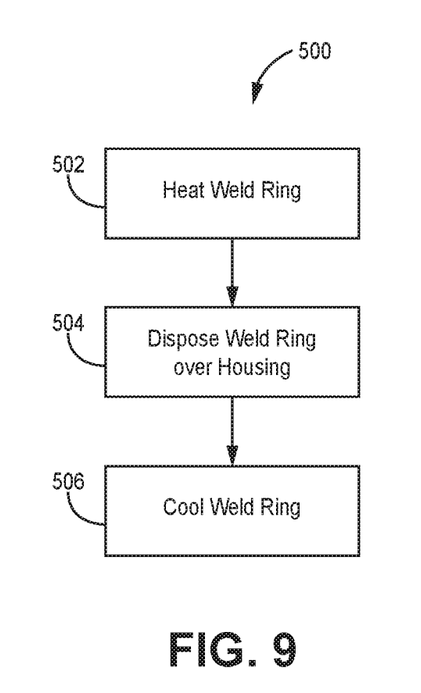
FIG. 9 is a flowchart of one embodiment of a method of compression molding a weld ring to a housing.

As mentioned herein, the weld rings 26, 30 of the housing assembly 4 of FIGS. 1-3 can be connected to the transparent portion 22 and the opaque portions 18, 20 using any suitable technique or techniques. For example, FIG. 9 is a flowchart of one embodiment of a method 500 of compression bonding one or both of the weld rings 26, 30 onto the outer surface 23 of the transparent portion 22 of the housing 12. Although described in reference to the hermetically-sealed package 10 of FIGS. 1-3, the method 500 can be utilized to form any suitable hermetically sealed package or housing assembly (e.g., housing assembly 100 of FIG. 4). The method includes compression bonding the weld ring (e.g., first weld ring 26) to the outer surface 23 of the transparent portion 22 of the housing 12. Compression bonding the first weld ring 26 includes heating at least one of the weld ring and the transparent portion 22 using any suitable technique or techniques at 502. In one or more embodiments, the materials utilized to form the weld ring 26 and the transparent portion 22 can have differing coefficients of thermal expansion such that the weld ring expands to a greater extent than that of the transparent portion.

The weld ring 26 can be heated to any suitable temperature such that the inner diameter of the weld ring increases until it is greater than an outer diameter of a portion of the outer surface 23 of the transparent portion 22 of the housing 12 upon which the weld ring will be placed. In one or more embodiments, the first weld ring 26 can be heated to a temperature of at least 300° C. and no greater than 800° C. At 504, the first weld ring 26 is disposed over the outer surface 23 of the transparent portion 22 of the housing 12. In one or more embodiments, the first weld ring 26 can be slid over the outer surface 23 of the transparent portion 22 until the weld ring is in the desired position. Further, in one or more embodiments, one or both of the first weld ring 26 and the transparent portion 22 can include one or more flanges as described herein. At 506, the first weld ring 26 is cooled such that the inner diameter of the weld ring contracts and the weld ring comes into contact with the outer surface 23 of the transparent portion 22, hermetically sealing the weld ring to the transparent portion. Pressure can be applied to an end surface of the first weld ring 26 to constrain maintain contact between the first weld ring and the transparent portion 23 as the first weld ring cools. In one or more embodiments, a metal layer can be disposed on the outer surface 23 of the transparent portion 22 of the housing 12 prior to disposing the first weld ring 26 over the outer surface of the transparent portion such that metal layer is disposed between the weld ring and the outer surface. The metal layer can assist in hermetically sealing the weld ring 26 to the transparent portion 22 of the housing 12. The metal layer can include any suitable material or materials as described herein.

In one or more embodiments, a second weld ring (e.g. second weld ring 30) can be compression bonded to the outer surface 23 of the transparent portion 22 of the housing 12, where the first weld ring 26 is compression bonded adjacent to the first end 24 of the transparent portion of the housing and the second weld ring is compression bonded adjacent to the second end 28 of the transparent portion. Any suitable technique or techniques can be utilized to compression bond the second weld ring 30 to the transparent portion 22, e.g., the same techniques utilized to compression bond the first weld ring 26 to the transparent portion. The first weld ring 26, transparent portion 22, and second weld ring 30 can be disposed over a rod and heated such that the rings and the transparent portion remain axially aligned while compression bonding occurs.

Returning to FIGS. 1-3, the package can include one or more external contacts disposed on or in such portions. In one or more embodiments, one or both of the opaque portions 18, 20 can be external contacts. In the embodiment illustrate in FIGS. 1-3, the package 10 includes a first external contact 42, a second external contact 44, and a third external contact 46. The external contacts 42, 44, 46 can be disposed in any suitable location on or adjacent to the transparent portion 22, the first opaque portion 18, the second opaque portion 20, or two or more of the transparent portion and the first and second opaque portions of the housing 12. As illustrated in FIGS. 1-3, the first external contact 42 is disposed at the first end 14 of the housing 12 such that it is connected to the first opaque portion 18. Further, the second external contact 44 is disposed at the second end 16 of the housing 12. And the third external contact 46 is disposed on or in the second opaque portion 20 of the housing 12. In one or more embodiments, the second opaque portion 20 of the housing 12 can provide the third external contact 46, e.g., the second opaque portion can include conductive material to provide the third external contact. In one or more embodiments, the second external contact 44 can be electrically isolated from the third external contact 46 by an electrically insulative material 48 disposed between the second external contact and the third external contact. The electrically insulative material 48 can include any suitable material or materials that can isolate the second external contact 44 from the third external contact 46.

The external contacts 42, 44, 46 can include any suitable conductive material or materials, e.g., copper, silver, titanium, niobium, zirconium, tantalum, stainless steel, platinum, iridium, or combinations thereof. In one or more embodiments, the external contacts 42, 44, 46 can include two or more materials, e.g., bi-metals, clad laminates, etc. The external contact 42, 44, 46 can include the same material or different materials.

The package 10 can include an electronic device 36 disposed within the housing 12 in any suitable location such that it is electrically connected to the power source 32. As illustrated in FIGS. 1-3, the electronic device 36 is disposed at least partially within the transparent portion 22 of the housing 12. In one or more embodiments, additional electronic devices can be disposed within at least one of the first and second opaque portions 18, 20 of the housing 12.

Electronic device 36 can include any suitable component or components, electronic circuitry, and one or more conductors that electrically connect the components and circuitry to each other. In the embodiment illustrated in FIGS. 1-3, electronic device 36 includes components 52 disposed on a substrate 53. The components 52 can each include any suitable component or electronic circuitry, e.g., capacitors, transistors, integrated circuits, including controllers and multiplexers, sensors, etc. Further, any suitable number of components 52 can be disposed on the substrate 53. In one or more embodiments, the electronic device 36 can be electrically connected to other electronic circuitry or devices disposed on or adjacent to the substrate 53 or within the housing 12.

Any suitable technique or techniques can be utilized to dispose the components 52 on the substrate 53. In one or more embodiments, the components 52 can be formed on or in the substrate 53. In one or more embodiments, the components 52 can be formed separately and then attached to the substrate 53 using any suitable technique or techniques, e.g., a bond can be formed between each component and the substrate.

As mentioned herein, the electronic device 36 can include one or more sensors, e.g., one or more optical sensors. In one or more embodiments, the one or more sensors can be disposed at least partially within the transparent portion 22 of the housing 12 such that the optical sensor can detect one or more external conditions, e.g., from a patient when the package 10 is disposed within the patient. For example, the electronic device 36 can include an infrared or near-infrared oxygen sensor that can detect through the housing 12 the oxygen level of the blood of the patient. The electronic device 36 can be electrically connected to one or more the external contacts 42, 44, 46 using any suitable technique or techniques.

Further, the package 10 includes the power source 32 disposed in the second opaque portion 20 of the housing 12. The package 10 can include any suitable number of power sources 32. The power source 32 can include any suitable power source or combination of power sources, e.g., one or more batteries, capacitors, inductive-coupled energy devices, photovoltaic devices, betavoltaic devices, alphavoltaic devices, and thermo-electric devices. Further, the power source 32 can be disposed in any suitable location within the housing 12. The power source 32 can be electrically connected to the electronic device 36 and the inductive coil 34 using any suitable technique or techniques. In one or more embodiments, the power source 32 can form one or more portions of the housing 12. For example, in the embodiment illustrated in FIGS. 1-3, the power source 323 forms the second opaque portion 20

The package 10 can also include one or more tines 50 that are disposed in any suitable location on the housing 12. In one or more embodiments, one or more tines 50 can be connected to the first opaque portion 18 of the housing 12 adjacent to the first end 14 of the housing. The tines 50 can be utilized to anchor the package 10 to tissue within a patient such that the package remains in the desired location after implantation. The tines 50 can take any suitable shape or shapes. Further, the package 10 can include any suitable number of tines 50. The tines 50 can include any suitable material or materials, e.g., the same materials described herein regarding the external contacts 42, 44, 46. In such embodiments, the tines 50 can be electrically connected to an external contact using any suitable technique or techniques. In one or more embodiments, the tines 50 can be attached to the external contact 42 using any suitable technique or techniques. In one or more embodiments, the tines 50 can be electrically insulative.

The package 10 can also include the inductive coil 34. The inductive coil 34 can be utilized to provide inductive coupling to one or more external devices, e.g., one or more inductive power sources such as inductive charging system 606 of assembly 600 of FIG. 10. The inductive coil 34 can include any suitable inductive device. The inductive coil 34 can be disposed in any suitable location on or within the housing 12. In one or more embodiments, the inductive coil 34 is disposed at least partially within the transparent portion 22 of the housing 12. The term "at least partially within" means that at least a portion of the inductive coil 34 is disposed within the transparent portion 22. In one or more embodiments, one or more portions of the inductive coil 34 can be disposed in one or both of the first and second opaque portions 18, 20. In one or more embodiments, the entire inductive coil 34 can be disposed within the transparent portion 22 of the housing 12.

As shown in FIG. 1, the inductive coil 34 is disposed on an inner surface 25 of the transparent portion 22 of the housing 12. The inductive coil 34 can take any suitable shape or shapes and have any suitable dimensions. Further, the inductive coil 34 can include any suitable conductive material or materials, e.g., the same materials described herein regarding external contacts 42, 44, 46 of package 10 of FIGS. 1-3. Although shown as disposed on the inner surface 25 of the transparent portion 22, the inductive coil 34 can be disposed on the outer surface 23 of the transparent portion 22, or on both the inner surface and the outer surface of the transparent portion. Further, the inductive coil 34 can include any suitable number of conductors, e.g., 1, 2, 3, 4, or more discrete conductors.

The inductive coil 34 can be electrically connected to one or more components 52 or power sources of the electronic device 36 and the power source 32 disposed within the housing 12 of the package 10 using any suitable technique or techniques. For example, if the inductive coil 34 is disposed on the outer surface 23 of the transparent portion 22, a via or vias can be formed between the outer surface and the inner surface 25 of the transparent portion. Conductive material can be disposed within such via or vias that electrically connects the inductive coil 34 to the electronic device. The inductive coil 34 can be electrically connected to the vias using any suitable technique or techniques. In embodiments where the inductive coil 34 is disposed on the inner surface 25 of the transparent portion 22, the coil can be electrically connected to the electronic device 36 and the power source 32 using any suitable technique or techniques, e.g., a lead wire or wires can be connected to the conductor and the electronic device.

Figure 10:
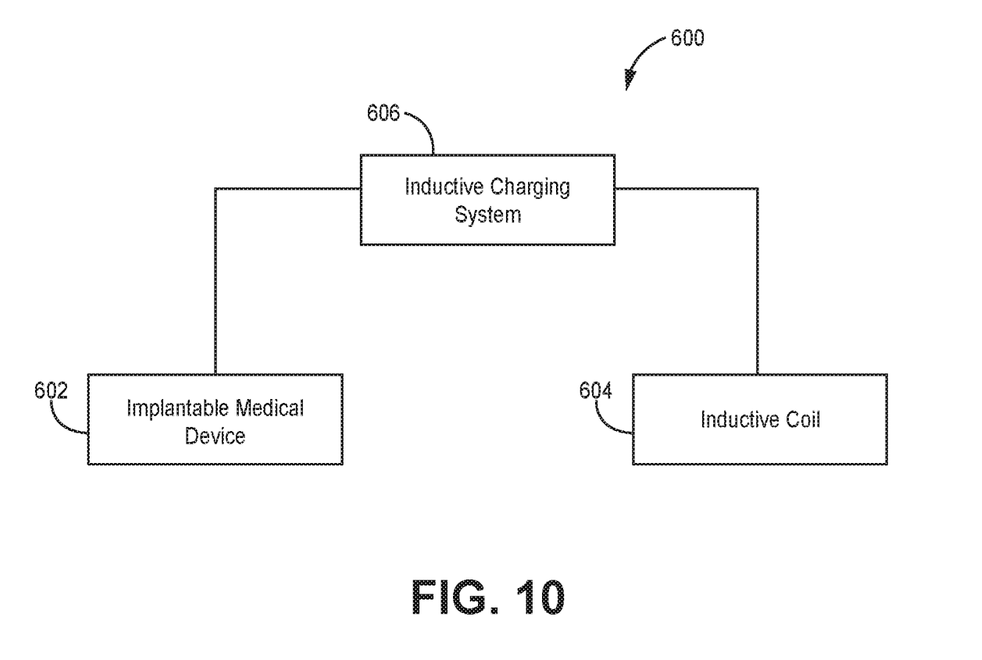
FIG. 10 is a schematic view of one embodiment of an implantable medical device assembly.

In embodiments where the hermetically sealed package 10 includes an inductive coil 34, the package can be a part of any suitable system or assembly that is adapted to provide energy to the package once the package is implanted in a patient. For example, FIG. 10 is a schematic view of one embodiment of a hermetically sealed package assembly 600. The assembly 600 includes an implantable medical device 602. The implantable medical device 602 can include any suitable device or devices. In one or more embodiments, the implantable medical device 602 can include a hermetically sealed package, e.g., hermetically sealed package 10 of FIGS. 1-3. The assembly 600 also includes an inductive coil 604 that is electrically connected to the implantable medical device 602. In one or more embodiments, the inductive coil 604 can be disposed within the implantable medical device 602. In one or more embodiments, the inductive coil 604 can be implanted within the patient separately from the implantable medical device 602 and electrically connected to the implantable medical device utilizing any suitable technique or techniques. In one or more embodiments, the inductive coil 604 can be disposed within the hermetically sealed package, e.g., the inductive coil 34 can be disposed within transparent portion 22 of housing 12 of the hermetically sealed package 10 of FIGS. 1-3. The assembly 600 also includes an inductive charging system 606. The inductive charging system 606 can be disposed adjacent to the patient such that it is adapted to provide a time-varying magnetic field (e.g., inductive field) that is capable of inductively charging the implantable medical device via the inductive coil 604. The inductive charging system 606 can be any suitable system, e.g., a flat planar coil, single axis Helmholtz coil, three-axis Helmholtz coil, etc.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed package comprising a housing that extends along a housing axis between a first end and a second end, wherein the housing comprises first and second opaque portions and a transparent portion disposed between the first and second opaque portions, wherein the first opaque portion is hermetically sealed to a first end of the transparent portion and the second opaque portion is hermetically sealed to a second end of the transparent portion, wherein at least one of the first and second opaque portions is hermetically sealed to the transparent portion by a weld ring.

2. The package of claim 1, wherein the first opaque portion is hermetically sealed to the first end of the transparent portion by the weld ring and the second opaque portion is hermetically sealed to the second end of the transparent portion by a second weld ring.

3. The package of claim 2, wherein at least one of the weld ring or the second weld ring is diffusion bonded to the transparent portion of the housing.

4. The package of claim 3, wherein at least one of the weld ring or the second weld ring is laser diffusion bonded to the transparent portion of the housing.

5. The package of claim 2, wherein at least one of the weld ring or the second weld ring is compression bonded to the transparent portion of the housing.

6. The package of claim 1, wherein the transparent portion of the housing is substantially transmissive to electromagnetic radiation having a frequency in a range of 10 kHz to 20 MHz.

7. The package of claim 1, further comprising an inductive coil disposed at least partially within the transparent portion of the housing.

8. The package of claim 1, wherein the first opaque portion of the housing comprises an external contact adapted to provide an electrical signal to tissue of a patient.

9. The package of claim 1, further comprising an external contact hermetically sealed to the second opaque portion of the housing.

10. The package of claim 1, wherein the housing comprises an elliptical cross-section in a plane orthogonal to the housing axis.

11. The package of claim 1, further comprising a tine connected to the first opaque portion of the housing adjacent to the first end of the housing.

12. The package of claim 1, wherein the transparent portion of the housing comprises a ceramic material.

13. The package of claim 1, wherein at least one of the first and second opaque portions of the housing comprises a ceramic material.

14. A housing assembly, comprising:
a housing comprising an outer surface and an inner surface and extending along a housing axis between a first end and a second end; and
a weld ring compression bonded to the outer surface of the housing at the first end and a second weld ring compression bonded to the outer surface of the housing at the second end, wherein the weld ring and the second weld ring are hermetically-sealed to the outer surface of the housing.

15. The assembly of claim 14, further comprising a diffusion layer disposed between the weld ring and the outer surface of the housing that is formed when the weld ring is compression bonded to the outer surface of the housing.

16. The assembly of claim 14, wherein the housing comprises a ceramic material.

17. The assembly of claim 14, wherein at least a portion of the housing is substantially transmissive to electromagnetic radiation having a frequency in a range of 10 kHz to 20 MHz.

18. The assembly of claim 14, wherein the housing further comprises a flange disposed adjacent to the first end of the housing, wherein the weld ring is disposed over the flange.

19. The assembly of claim 18, wherein the flange comprises a tapered portion, wherein the weld ring comprises a flange that comprises a tapered portion, wherein the tapered portion of the flange of the housing is adapted to receive the tapered portion of the flange of the weld ring.

20. The assembly of claim 18, wherein the housing further comprises a second flange disposed adjacent to the second end of the housing, wherein the second weld ring is disposed over the second flange.

* * * * *